(12) United States Patent
Takada

(10) Patent No.: US 11,078,129 B2
(45) Date of Patent: Aug. 3, 2021

(54) METHOD FOR PRODUCING OLEFIN

(71) Applicant: KAO CORPORATION, Tokyo (JP)

(72) Inventor: Shingo Takada, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/645,722

(22) PCT Filed: May 29, 2018

(86) PCT No.: PCT/JP2018/020488
§ 371 (c)(1),
(2) Date: Mar. 9, 2020

(87) PCT Pub. No.: WO2019/053956
PCT Pub. Date: Mar. 21, 2019

(65) Prior Publication Data
US 2020/0299211 A1 Sep. 24, 2020

(30) Foreign Application Priority Data

Sep. 12, 2017 (JP) ............................. JP2017-174794

(51) Int. Cl.
*C07C 1/24* (2006.01)
*C07C 11/02* (2006.01)

(52) U.S. Cl.
CPC ................ *C07C 1/24* (2013.01); *C07C 11/02* (2013.01); *C07C 2521/04* (2013.01)

(58) Field of Classification Search
CPC ......... C07C 1/24; C07C 11/02; C07C 309/20; C07C 2521/04; C07C 1/20; C07C 11/04; B01J 21/04; B01J 21/12
See application file for complete search history.

(56) References Cited

U.S. PATENT DOCUMENTS 4,302,357 A 11/1981 Kojima et al.
9,968,914 B2 * 5/2018 Takada ................. B01J 35/1061
(Continued)

FOREIGN PATENT DOCUMENTS

CN 103508476 A 1/2014
EP 2 990 395 A1 3/2016
(Continued)

OTHER PUBLICATIONS

Asaoka, Functional Development through Microstructure Control: Imparting Response Selectivity Using Microstructure Control of Catalyst Carriers. Ceramics Japan: Bulleting of the Ceramic Society of Japan, in particular, Section 2.1 Response Selectivity, ISSN 0009-031X, 1998, vol. 33, No. 4, pp. 299-302.
(Continued)

*Primary Examiner* — Sharon Pregler
(74) *Attorney, Agent, or Firm* — Birch, Stewart, Kolasch & Birch, LLP.

(57) ABSTRACT

The present invention relates to a method for producing an olefin with a high yield for a short reaction time in a dehydration reaction of an aliphatic alcohol. The present invention provides a method for producing an olefin, including subjecting an aliphatic alcohol having 6 or more carbon atoms to a dehydration reaction in the presence of an aluminum oxide catalyst, wherein an average pore diameter of the aluminum oxide catalyst is 12.5 nm or more and 20.0 nm or less.

16 Claims, 1 Drawing Sheet

(56) References Cited

U.S. PATENT DOCUMENTS

| | | | |
|---|---|---|---|
| 2008/0058572 | A1 | 3/2008 | Fernandez et al. |
| 2012/0220808 | A1 | 8/2012 | Takada |
| 2015/0353442 | A1 | 12/2015 | Takada |
| 2017/0022124 | A1 | 1/2017 | Aribert et al. |

FOREIGN PATENT DOCUMENTS

| | | | |
|---|---|---|---|
| JP | 59-40057 B2 | 9/1984 | |
| JP | 2008-56671 A | 3/2008 | |
| WO | WO 2011/052732 A1 | 5/2011 | |
| WO | WO 2014/175359 A1 | 10/2014 | |

OTHER PUBLICATIONS

International Search Report (PCT/ISA/210) issued in PCT/JP2018/020488, dated Aug. 28, 2018.
Takahash et al., "Dehydration of 1-phenylethanol over solid acidic catalysts", The Canadian Journal of Chemical Engineering, 1988, vol. 66, No. 3, pp. 433-437, ISSN 1939-019X, in particular, p. 436, left column, paragraph [0002], Conclusions.
Extended European Search Report for European Application No. 18856841.4, dated May 14, 2021.
May et al., "Tailored mesoporous alumina prepared from different aluminum alkoxide precursors," Journal of Porous Materials, vol. 14, No. 2, 2007 (published online Jan. 26, 2007), pp. 159-164, XP019504813.

\* cited by examiner

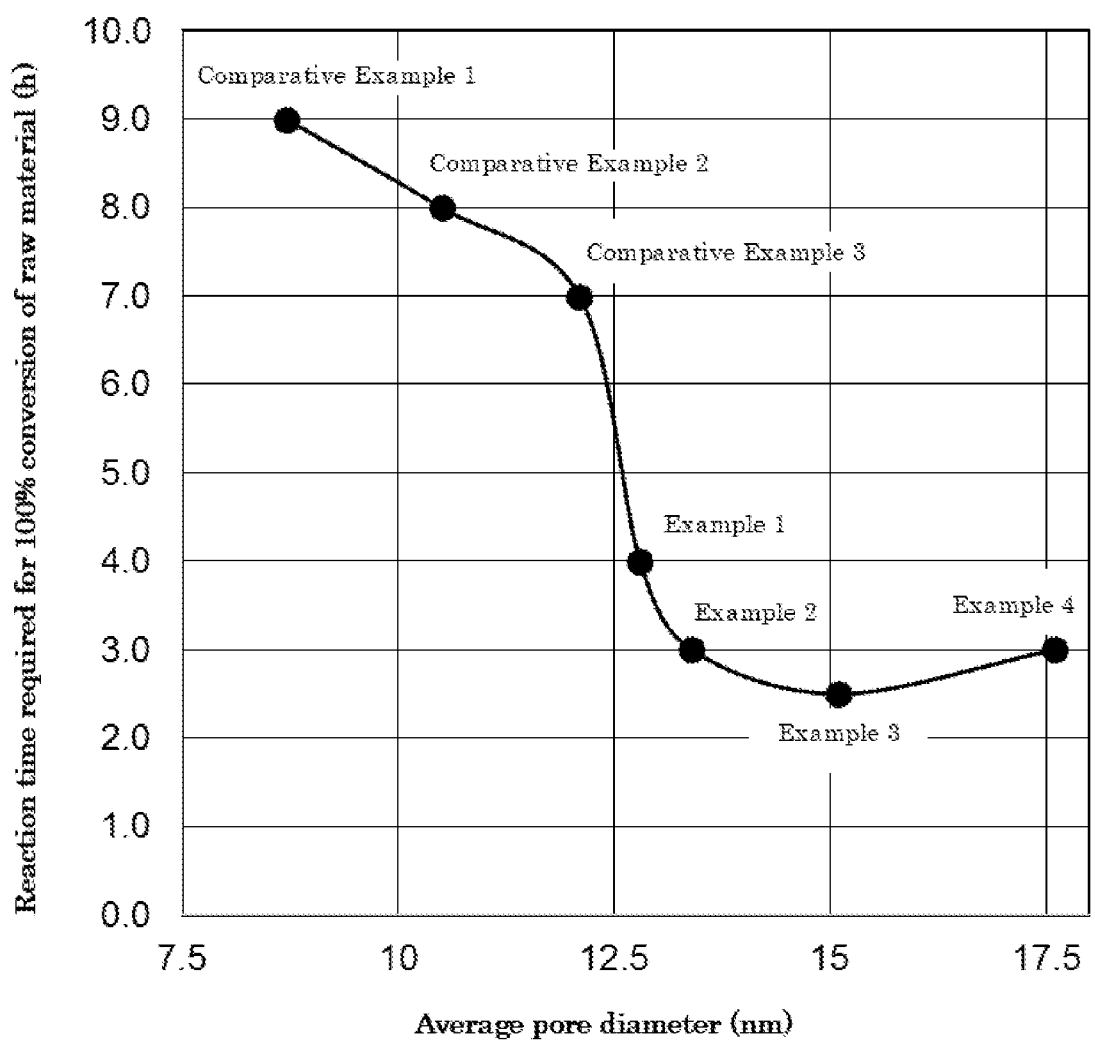

METHOD FOR PRODUCING OLEFIN

FIELD OF THE INVENTION

The present invention relates to a method for producing an olefin.

BACKGROUND OF THE INVENTION

There are known various methods for producing olefin compounds by dehydration reaction of alcohols. For example, PTL 1 (JP 2008-56671 A) discloses a method for producing an olefin compound by subjecting a tertiary alcohol to a dehydration reaction in a gas phase at a temperature of 200 to 400° C. in the presence of an aluminosilicate as a solid catalyst.

In addition, PTL 2 (JP 59-40057 B) discloses a method for producing ethylene by subjecting ethanol to a dehydration reaction in a gas phase in the presence of a catalyst prepared by adding a phosphate to active alumina.

Furthermore, PTL 3 (WO 2011/052732 A) describes that a liquid phase dehydration reaction of an aliphatic primary alcohol is performed by using a catalyst, such as γ-alumina, in a specified amount of a weak acid.

SUMMARY OF THE INVENTION

A method for producing an olefin of the present invention is a method for producing an olefin, including subjecting an aliphatic alcohol having 6 or more carbon atoms to a dehydration reaction in the presence of an aluminum oxide catalyst, wherein an average pore diameter of the aluminum oxide catalyst is 12.5 nm or more and 20.0 nm or less.

BRIEF DESCRIPTION OF THE DRAWING

FIG. 1 is a graph showing a relation between an average pore diameter of a catalyst and a reaction time for which a conversion of a raw material alcohol reaches 100%, with respect to Examples 1 to 4 and Comparative Examples 1 to 3.

DETAILED DESCRIPTION OF THE INVENTION

In the gas phase reaction represented by the method described in PTL 1 or 2, it is needed to evaporate all of the raw materials, and in particular, with respect to a long-chain aliphatic alcohol having a high boiling point, the energy consumption is large, and the foregoing method is disadvantageous from the cost standpoint. Furthermore, in the aluminosilicate catalyst used in PTL 1, branching owing to alkyl rearrangement and multimerization of the olefin are liable to concur, so that a lowering of the yield of the aimed reaction product is of a problem. In addition, PTL 2 merely describes to suppress deposition of carbonaceous substances but does not describe at all the suppression of branching owing to alkyl rearrangement or multimerization of the olefin.

The olefins produced by the method described in PTL 3 contain merely a small amount of by-products produced owing to production of multimerization or branching. However, it has been further demanded to develop a method for producing olefins with a still higher efficiency.

The present invention relates to a method for producing an olefin for a short reaction time with a high efficiency through a dehydration reaction of an aliphatic alcohol.

The present inventor has found that by performing a dehydration reaction of an aliphatic alcohol in the presence of an aluminum oxide catalyst having a specified average pore diameter, it is possible to produce an olefin with a high yield for a short reaction time.

That is, the present invention provides a method for producing an olefin, including subjecting an aliphatic alcohol having 6 or more carbon atoms to a dehydration reaction in the presence of an aluminum oxide catalyst, wherein an average pore diameter of the aluminum oxide catalyst is 12.5 nm or more and 20.0 nm or less.

In accordance with the present invention, a method for producing an olefin with a high yield for a short reaction time with a high efficiency in a dehydration reaction of an aliphatic alcohol.

The present inventor has found that on producing an olefin through a dehydration reaction of an aliphatic alcohol having 6 or more carbon atoms, by using an aluminum oxide catalyst having a specified average pore diameter, the reaction time is conspicuously shortened, and the olefin is obtained with a high yield.

Although a detailed reason why the aforementioned effect is obtained is not elucidated yet, the following may be considered. It may be considered that in the dehydration reaction of the aliphatic alcohol having 6 or more carbon atoms, the olefin is obtained through etherification owing to intermolecular dehydration. In such a reaction, as compared with the etherification reaction owing to intermolecular dehydration, the activation energy of olefination reaction of an ether compound is large, and the olefination reaction of an ether compound becomes a rate determining reaction.

Here, the ether compound is one having 12 or more carbon atoms and having a relatively large molecular size. In such a reaction, it may be presumed that the aluminum catalyst having a specified average pore diameter as mentioned above has an especially high catalytic ability.

In the following description, what the catalytic ability or catalytic activity is high means the fact that not only the reaction time is short, but also the olefin can be produced with a high yield.

[Aluminum Oxide Catalyst]

In the present invention, an aluminum oxide catalyst (hereinafter also referred to simply as "aluminum oxide") is used as the catalyst of dehydration reaction.

From the viewpoint of acquiring high catalytic activity, the aluminum oxide ($Al_2O_3$) is preferably γ-alumina.

From the viewpoint of acquiring high catalytic activity, the average pore diameter of the aluminum oxide is 12.5 nm or more, preferably 13.0 nm or more, and more preferably 13.5 nm or more. In addition, from the viewpoint of acquiring easiness of availability and high catalytic ability, the average pore diameter of the aluminum oxide is 20.0 nm or less, preferably 18.0 nm or less, and more preferably 16.0 nm or less.

The average pore diameter of the aluminum oxide catalyst is measured by the method described in the section of Examples.

From the viewpoint of acquiring high catalytic activity, the pore diameter of the aluminum oxide is preferably 5.0 nm or more, more preferably 6.0 nm or more, and still more preferably 8.0 nm or more, and from the viewpoint of acquiring easiness of availability and high catalytic ability, it is preferably 25.0 nm or less, more preferably 20.0 nm or less, and still more preferably 18.0 nm or less.

From the viewpoint of acquiring high catalytic activity, easiness of availability, and high catalytic ability, the distribution range of the pore diameter of the aluminum oxide is preferably 5.0 nm or more and 25.0 nm or less, more preferably 6.0 nm or more and 20.0 nm or less, and still more preferably 8.0 nm or more and 18.0 nm or less.

The pore diameter of the aluminum oxide may be distributed outside the aforementioned preferred distribution range so far as the average pore diameter of the aluminum oxide catalyst falls within the range prescribed in the present invention.

From the viewpoint of acquiring high catalytic activity, the pore volume of the aluminum oxide is preferably more than 0.50 cm$^3$/g, and more preferably 0.55 cm$^3$/g or more, and it is preferably 2.0 cm$^3$/g or less, more preferably 1.5 cm$^3$/g or less, still more preferably 1.2 cm$^3$/g or less, yet still more preferably 1.0 cm$^3$/g or less, and even yet still more preferably 0.7 cm$^3$/g or less.

From the viewpoint of acquiring high catalytic activity, the BET specific surface area of the aluminum oxide is preferably 190 m$^2$/g or more, and more preferably 200 m$^2$/g or more. In addition, from the viewpoint of acquiring durability of catalyst and high catalytic activity, the BET specific surface area of the aluminum oxide is preferably 500 m$^2$/g or less, more preferably 400 m$^2$/g or less, still more preferably 300 m$^2$/g or less, yet still more preferably 250 m$^2$/g or less, and even yet still more preferably 220 m$^2$/g or less.

The pore volume and the BET specific surface area of the aluminum oxide are measured by the method described in the section of Examples.

Although the aluminum oxide may be prepared by any methods, from the viewpoint of preparing the aluminum oxide having a desired average pore diameter and acquiring high catalytic activity, the preparation method is preferably a precipitation method, a sol-gel method, an alkoxide method, a pH swing method, or the like, and more preferably a pH swing method.

It is preferred that the resulting aluminum oxide is calcined, and from the viewpoint of acquiring high catalytic activity, the calcination temperature is preferably 400° C. or higher, more preferably 450° C. or higher, and still more preferably 480° C. or higher, and it is preferably 900° C. or lower, more preferably 850° C. or lower, and still more preferably 800° C. or lower.

From the viewpoint of acquiring high catalytic activity, the calcination time is preferably 1 hour or more, more preferably 2 hours or more, and still more preferably 3 hours or more, and it is preferably 10 hours or less, more preferably 7 hours or less, and still more preferably 5 hours or less.

The atmosphere for calcination is not particularly limited, and the calcination can be performed in an inert gas atmosphere, in an oxidizing atmosphere, or in a reducing atmosphere. In addition, the calcination may also be performed in a closed condition or in a gas-flowing condition. In the present invention, from the viewpoint of catalytic activity, the atmosphere is preferably a gas-flow condition of air or oxygen.

As one example of a method of controlling the average pore diameter of the aluminum oxide catalyst, there is exemplified a method by the pH swing method. The pH swing method is one kind of the precipitation method and is a method in which in the precipitation method using an aluminum salt and an inorganic base as raw materials, aqueous solutions of the both raw materials are alternately added to form a precipitate while raising or lowering the pH.

For example, in the case of using aluminum chloride and ammonia as the raw materials, when ammonia water is continued to be gradually added to the aluminum chloride aqueous solution, the pH rises and exceeds 9. Then, when the aluminum chloride aqueous solution is continued to be gradually added, the pH drops and becomes less than 4.

In this way, by setting the pH change to a swing width falling outside the range of 4 to 9 that is the precipitate-forming pH of aluminum, a fine crystal of aluminum formed within the range of 4 to 9 that is the precipitate-forming pH is dissolved and used for crystal growth on the occasion when the pH falls within the precipitate-forming pH, and the crystal particle diameter can be gradually increased. On that occasion, by regulating the temperature, the retention time, the raw material concentrations, the swing width of pH, the number of swings, and the like, the crystal particle diameter, the specific surface area, and the pore structure can be regulated, and the crystal particle diameter after calcination or the pore diameter that is a gap between the crystal particles, the pore volume, the specific surface area, and the like can be regulated.

The synthesis of the aluminum oxide (alumina) by the pH swing method is described in detail in literatures, for example, JP 1-16773 B, JP 2-56283 B, JP 56-120508 B, JP 57-44605 B, JP 2003-292820 A, JP 56-115638 A, and "Ceramics", Vol. 33, No. 4, pp. 299-302 (1998), and these can be made by reference.

In the present invention, the catalyst thus obtained is in an aggregated state, and thus, it is preferred to use it after being appropriately pulverized into the form of a powder or a granule, or molded into noodles, pellets, or the like.

In the case of molding into noodles, it is preferred to perform molding into a molded article in a noodle-like form through extrusion molding, and in the case of molding into pellets, it is preferred to perform molding into a molded article in a pellet-like form through tablet making. In the case of molding into the form of granules, noodles, pellets, or the like, the molded article may be produced by kneading together with a small amount of a binder and molding the resulting mixture after being optionally dried, followed by calcination.

Examples of the binder which is used herein include polymer compounds and inorganic compounds. Examples of the polymer compound include a cellulose-based resin, such as carboxymethyl cellulose and hydroxyethyl cellulose; a fluorine-based resin, such as polytetrafluoroethylene and polyvinylidene fluoride; a urethane resin; an epoxy resin; a polyester resin; a phenol resin; a melamine resin; a silicone resin; polycarbotitanium; and polytitanocarbosilane. In addition, example of the inorganic compound include an inorganic compound sol of silica, alumina, or the like. From the viewpoint of productivity of the catalyst, the binder is preferably a polymer compound.

In the case where the aluminum oxide catalyst is a powder, from the viewpoint of easiness of catalyst recovery, the average particle diameter of the powder is preferably 1 µm or more, more preferably 5 µm or more, still more preferably 10 µm or more, yet still more preferably 20 µm or more, and even yet still more preferably 30 µm or more. In addition, from the viewpoint of acquiring high catalytic activity, the average particle diameter of the powder is preferably 300 µm or less, more preferably 250 µm or less, still more preferably 200 µm or less, yet still more preferably 150 µm or less, even yet still more preferably 100 µm or less, even still more preferably 50 µm or less, and even still more further preferably 37 µm or less.

The average particle diameter is measured by the method described in the section of Examples.

In the case where the aluminum oxide catalyst is a granule, from the viewpoint of easiness of catalyst recovery, the average particle diameter of the granule is preferably 0.2 mm or more, more preferably 0.4 mm or more, and still more preferably 0.6 mm or more, and from the viewpoint of acquiring high catalytic activity, the average particle diameter of the granule is preferably 2.0 mm or less, more preferably 1.3 mm or less, and still more preferably 0.8 mm or less.

In the case where the aluminum oxide catalyst is a granule, the average particle diameter of the granule is measured in the following manner. That is, using sieves of 2,000, 1,400, 1,000, 710, 500, 355, 250, 180, 125, 90, 63, and 45 μm as prescribed by JIS Z8801-1 (established on May 20, 2000 and finally revised on Nov. 20, 2006), vibration is performed for 5 minutes, a 50% average diameter is calculated based on undersize mass distribution determined by the sieving method, and the calculated value is designated as an average particle diameter. Specifically, using sieves of 2,000, 1,400, 1,000, 710, 500, 355, 250, 180, 125, 90, 63, and 45 μm as prescribed by JIS Z8801-1 (established on May 20, 2000 and finally revised on Nov. 20, 2006), the sieves are stacked on a receiving tray in the order beginning from those sieves having smaller sieve openings; 100 g of granules are added from the upper portion of the uppermost sieve having a size of 2,000 μm; and a lid is placed and attached to a rotating and tapping shaker machine (manufactured by HEIKO SEISAKUSHO, Ltd., tapping: 156 times/min, rolling: 290 times/min). The granules are vibrated for 5 minutes, and the masses of the granules remaining on each of the sieves and the receiving tray are measured, and a mass proportion (%) of the granules on each sieve is calculated. The mass proportions of the granules in the order beginning from the receiving tray to those sieves having smaller sieve openings are cumulated, and a particle diameter at which the sum total thereof is 50% is designated as the average particle diameter.

In the case where the aluminum oxide catalyst is in a noodle-like form, from the viewpoint of acquiring high catalytic activity, its average diameter is preferably 1.0 mm or more, more preferably 1.2 mm or more, and still more preferably 1.4 mm or more, and it is preferably 2.5 mm or less, more preferably 2.0 mm or less, and still more preferably 1.5 mm or less.

In the case where the aluminum oxide catalyst is in a noodle-like form, from the viewpoint of uniformity at the time of filling, its average length is preferably 8 mm or less, more preferably 6 mm or less, and still more preferably 4.5 mm or less, and from the viewpoint of acquiring high catalytic activity, the average length is preferably 2 mm or more, more preferably 3 mm or more, and still more preferably 3.5 mm or more.

The aforementioned average diameter and average length are measured with calipers.

In the case where the aluminum oxide catalyst is in a pellet-like form, from the viewpoint of acquiring high catalytic activity, its average diameter and average height are each preferably 1.5 mm or more, more preferably 2.0 mm or more, and still more preferably 2.5 mm or more, and they are each preferably 5.0 mm or less, more preferably 4.0 mm or less, and still more preferably 3.0 mm or less.

The aforementioned average diameter and average height are measured with calipers.

[Raw Material Alcohol]

In the present invention, an aliphatic alcohol having 6 or more carbon atoms is used as the raw material alcohol.

The raw material alcohol is preferably a straight-chain aliphatic alcohol having 6 or more carbon atoms. Here, the straight-chain aliphatic alcohol is a compound in which at least one hydroxy group is substituted on a straight-chain aliphatic hydrocarbon.

In the present invention, from the viewpoint of reactivity, the raw material alcohol is preferably one in which one or two hydroxy groups are substituted on a straight-chain aliphatic hydrocarbon, and preferably one in which one hydroxy group is substituted on a straight-chain aliphatic hydrocarbon. That is, the raw material alcohol is preferably a straight-chain or branched monool (monoalcohol) or a straight-chain or branched diol, more preferably a straight-chain or branched monool (monoalcohol), still more preferably a straight-chain monool, and yet still more preferably a saturated straight-chain monool.

A substitution position of the hydroxy group on the aliphatic hydrocarbon is not particularly limited. The aliphatic alcohol may be a primary alcohol in which the hydroxy group is substituted on the carbon atom of the end of the aliphatic hydrocarbon, or may be a secondary alcohol in which the hydroxy group is substituted on the carbon atom other than the end of the aliphatic hydrocarbon. The substitution position of the hydroxy group on the straight-chain aliphatic alcohol and the saturated straight-chain aliphatic alcohol is also the same. Of these, the aliphatic alcohol is preferably a primary alcohol, more preferably a straight-chain primary aliphatic alcohol, and still more preferably a saturated straight-chain primary alcohol, in which the hydroxy group is substituted on the carbon atom of the end thereof.

The aliphatic alcohol is preferably a saturated aliphatic alcohol, and more preferably a saturated straight-chain aliphatic alcohol.

The carbon number of each of the aforementioned aliphatic alcohols is 6 or more, and from the viewpoint of usefulness of the resulting olefin, the carbon number is preferably 8 or more, more preferably 12 or more, and still more preferably 14 or more, and it is preferably 22 or less, more preferably 20 or less, and still more preferably 18 or less.

From the viewpoint of usefulness of the olefin, as a specific example of the raw material alcohol, one or more selected from 1-dodecanol, 1-tridecanol, 1-tetradecanol, 1-pentadecanol, 1-hexadecanol, 1-heptadecanol, 1-octadecanol, 1-nonadecanol, and 1-eicosanol are preferred.

[Organic Solvent]

In the production method of the present invention, from the viewpoint of productivity, it is desired that an organic solvent is not substantially used. However, in the production method of the present invention, an organic solvent may be used, if desired. The organic solvent which can be used in the present invention is not particularly limited so far as it is a liquid at the reaction temperature, is compatible with the raw material alcohol and the olefin that is a product, and does not hinder the reaction, and the organic solvent may also be in the form of a mixture. In addition, one which after the reaction, is able to be separated from the product utilizing a difference in boiling point, is preferred.

As the organic solvent which can be used in the present invention, a hydrocarbon-based organic solvent, such as a saturated aliphatic hydrocarbon, an unsaturated aliphatic hydrocarbon, and an aromatic hydrocarbon, is preferred.

The saturated aliphatic hydrocarbon may be either a straight-chain hydrocarbon or a branched hydrocarbon.

Specific examples of the saturated aliphatic hydrocarbon include compounds having 10 or more and 35 or less carbon atoms, such as tridecane, hexadecane, octadecene, eicosane, docosane, triacontane, and squalane.

The saturated aliphatic hydrocarbon may also be in the form of a mixture, such as liquid paraffin, a naphthene-based hydrocarbon, and an isoparaffin-based hydrocarbon. In addition, as the saturated aliphatic hydrocarbon, a solid paraffin that is kept in a solid state at a normal temperature but changed into a liquid state at the reaction temperature can also be used.

As the saturated aliphatic hydrocarbon, oligomers of propylene, isobutene, or the like can also be used.

The unsaturated aliphatic hydrocarbon may be either a straight-chain hydrocarbon or a branched hydrocarbon.

Specific examples of the unsaturated aliphatic hydrocarbon include compounds having preferably 15 or more carbon atoms, and more preferably 25 or more carbon atoms, and preferably 35 or less carbon atoms, and more preferably 35 or less carbon atoms, such as eicosene, heneicosene, docosene, tricosene, and squalene. The unsaturated aliphatic hydrocarbon may also be in the form of a mixture.

Specific examples of the aromatic hydrocarbon include alkylbenzenes and alkylnaphthalenes, such as n-dodecylbenzene, n-tridecylbenzene, n-tetradecylbenzene, n-pentadecylbenzene, n-hexadecylbenzene, and diisopropylnaphthalene.

[Dehydration Reaction (Olefination Reaction)]

In the present invention, the phase state of the dehydration reaction (olefination reaction) between the aluminum oxide catalyst and the raw material alcohol is not particularly limited, and the reaction may be performed in a liquid phase or may be performed in a gas phase. Above all, the olefination reaction is preferably a liquid phase reaction. The liquid phase reaction refers to a reaction at a temperature equal to or lower than the boiling point of the raw material alcohol, namely at which the liquid phase is existent. In the case of the liquid phase reaction, the raw materials may not be necessarily evaporated entirely, the productivity is excellent, and the production cost can be suppressed. In addition, since multimerization of the olefin can be suppressed, the target product can be obtained with a high yield.

In the present invention, the reaction is not particularly limited with respect to the mode, and though it may be either a suspension bed reaction or a fixed bed reaction, it is preferably a suspension bed reaction.

The aforementioned reaction may be performed in an inert gas atmosphere of nitrogen or the like, or in a reducing atmosphere.

From the viewpoint of reactivity, the aforementioned reaction is preferably performed in an inert gas atmosphere. From the viewpoint of economy, the inert gas is preferably a helium gas, a nitrogen gas, or an argon gas, and more preferably a nitrogen gas.

The reaction in the method of the present invention is the dehydration reaction of an alcohol, and there is a concern that when by-produced water is accumulated in the reaction system, the reaction rate thereof is decreased. In consequence, in the case where the reaction is a suspension bed reaction, from the viewpoint of improving the reaction rate, in general, the reaction is preferably performed while removing the produced water outside the reaction system by introducing an inert gas, such as nitrogen and argon, into the reaction system with stirring under reduced pressure of 0.03 MPa or more and 0.09 MPa or less, or at atmospheric pressure.

In the case of a suspension bed reaction, from the viewpoint of reactivity, the amount of the catalyst used is preferably 0.1 part by mass or more, more preferably 0.5 part by mass or more, still more preferably 1 part by mass or more, and yet still more preferably 2 parts by mass or more, and from the viewpoint of purification after the reaction, it is preferably 20 parts by mass or less, more preferably 15 parts by mass or less, still more preferably 10 parts by mass or less, and yet still more preferably 5 parts by mass or less, based on 100 parts by mass of the raw material alcohol.

From the viewpoint of the yield of the target olefin, the reaction time is one such that the conversion of the raw material alcohol (alcohol conversion) reaches preferably 95% or more, more preferably 97% or more, and still more preferably 98% or more, and it is also preferred that the alcohol conversion is 100%. Such a reaction time may vary depending upon the reaction temperature, the kind of the organic solvent, the kind and the amount of the catalyst used, the kind of the raw material alcohol, and so on.

In the suspension bed reaction, from the viewpoint of reactivity, the reaction time is preferably 0.1 hour or more, more preferably 0.5 hour or more, and still more preferably 1 hour or more, and from the viewpoint of suppressing a side reaction, it is preferably 20 hours or less, more preferably 15 hours or less, and still more preferably 7 hours or less. As for the reaction time, the point of time when the temperature of the reaction system has reached a target temperature is designated as 0 hour.

In the fixed bed reaction, from the viewpoint of reactivity, the LHSV (liquid hourly space velocity) is preferably 10/h or less, more preferably 7/h or less, still more preferably 5/h or less, and yet still more preferably 3/h or less, and from the viewpoint of productivity, it is preferably 0.03/h or more, more preferably 0.05/h or more, still more preferably 0.1/h or more, and yet still more preferably 0.2/h or more.

From the viewpoint of reactivity and the viewpoint of suppressing a side reaction, such as multimerization, the reaction temperature is preferably a temperature equal to or lower than the boiling point of the raw material alcohol. From the viewpoint of reactivity, specifically, the reaction temperature is preferably 200° C. or higher, more preferably 220° C. or higher, still more preferably 240° C. or higher, and yet still more preferably 260° C. or higher, and from the viewpoint of suppressing a side reaction, it is preferably 350° C. or lower, more preferably 330° C. or lower, still more preferably 310° C. or lower, and yet still more preferably 290° C. or lower.

The reaction pressure is not particularly limited, and the reaction may be performed under any pressure of atmospheric pressure, reduced pressure, and elevated pressure. Above all, from the viewpoint of productivity and reactivity, the reaction pressure is preferably atmospheric pressure or reduced pressure, and more preferably atmospheric pressure.

In accordance with the production method of the present invention, the formation of a dimerized olefin (dimer) that is a by-product is suppressed, and a formation rate (yield) of the dimer is typically 7% or less, and preferably 5% or less.

The formation rate (yield) of the dimer is measured by the method described in the section of Examples.

In the present invention, only the olefin may be subjected to distillation and purification from the resulting reaction product obtained in the aforementioned method. The olefin having a high purity obtained through distillation purification is useful as a raw material or an intermediate of a surfactant, an organic solvent, a softener, a sizing agent, and the like.

In addition to the aforementioned embodiments, the present invention discloses the following methods for producing an olefin.

<1> A method for producing an olefin, including subjecting an aliphatic alcohol having 6 or more carbon atoms to a dehydration reaction in the presence of an aluminum oxide catalyst, wherein an average pore diameter of the aluminum oxide catalyst is 12.5 nm or more and 20.0 nm or less.

<2> The method for producing an olefin as set forth in the item <1>, wherein the aliphatic alcohol is preferably a primary alcohol or a secondary alcohol, and more preferably a primary alcohol.

<3> The method for producing an olefin as set forth in the item <1> or <2>, wherein the aliphatic alcohol is preferably a straight-chain or branched monool or a straight-chain or branched diol, more preferably a straight-chain or branched monool, still more preferably a straight-chain monool, and yet still more preferably a saturated straight-chain monool.

<4> The method for producing an olefin as set forth in any of the items <1> to <3>, wherein the aliphatic alcohol is preferably a straight-chain aliphatic alcohol, and more preferably a saturated straight-chain aliphatic alcohol.

<5> The method for producing an olefin as set forth in any of the items <1> to <4>, wherein the carbon number of the aliphatic alcohol is preferably 8 or more, more preferably 12 or more, and still more preferably 14 or more, and it is preferably 22 or less, more preferably 20 or less, and still more preferably 18 or less.

<6> The method for producing an olefin as set forth in any of the items <1> to <5>, wherein the carbon number of the aliphatic alcohol is 8 or more and 22 or less.

<7> The method for producing an olefin as set forth in any of the items <1> to <6>, wherein the carbon number of the aliphatic alcohol is 12 or more and 20 or less.

<8> The method for producing an olefin as set forth in any of the items <1> to <7>, wherein the carbon number of the aliphatic alcohol is 14 or more and 18 or less.

<9> The method for producing an olefin as set forth in any of the items <1> to <7>, wherein the aliphatic alcohol is one or more selected from 1-dodecanol, 1-tridecanol, 1-tetradecanol, 1-pentadecanol, 1-hexadecanol, 1-heptadecanol, 1-octadecanol, 1-nonadecanol, and 1-eicosanol.

<10> The method for producing an olefin as set forth in any of the items <1> to <9>, wherein the aluminum oxide catalyst is γ-alumina.

<11> The method for producing an olefin as set forth in any of the items <1> to <10>, wherein the average pore diameter of the aluminum oxide catalyst is preferably 13.0 nm or more, and more preferably 13.5 nm or more, and it is preferably 18.0 nm or less, and more preferably 16.0 nm or less.

<12> The method for producing an olefin as set forth in any of the items <1> to <11>, wherein the average pore diameter of the aluminum oxide catalyst is preferably 13.0 nm or more and 20.0 nm or less.

<13> The method for producing an olefin as set forth in any of the items <1> to <12>, wherein the average pore diameter of the aluminum oxide catalyst is preferably 13.0 nm or more and 18.0 nm or less.

<14> The method for producing an olefin as set forth in any of the items <1> to <13>, wherein the average pore diameter of the aluminum oxide catalyst is preferably 13.5 nm or more and 16.0 nm or less.

<15> The method for producing an olefin as set forth in any of the items <1> to <14>, wherein the pore volume of the aluminum oxide catalyst is preferably more than 0.50 cm$^3$/g, and more preferably 0.55 cm$^3$/g or more, and it is preferably 2.0 cm$^3$/g or less, more preferably 1.5 cm$^3$/g or less, still more preferably 1.2 cm$^3$/g or less, yet still more preferably 1.0 cm$^3$/g or less, and even yet still more preferably 0.7 cm$^3$/g or less.

<16> The method for producing an olefin as set forth in any of the items <1> to <15>, wherein the pore volume of the aluminum oxide catalyst is preferably more than 0.50 cm$^3$/g and 2.0 cm$^3$/g or less.

<17> The method for producing an olefin as set forth in any of the items <1> to <16>, wherein the pore volume of the aluminum oxide catalyst is preferably 0.55 cm$^3$/g or more and 1.5 cm$^3$/g or less.

<18> The method for producing an olefin as set forth in any of the items <1> to <17>, wherein the pore volume of the aluminum oxide catalyst is preferably 0.55 cm$^3$/g or more and 1.2 cm$^3$/g or less.

<19> The method for producing an olefin as set forth in any of the items <1> to <18>, wherein the pore volume of the aluminum oxide catalyst is preferably 0.55 cm$^3$/g or more and 1.0 cm$^3$/g or less.

<20> The method for producing an olefin as set forth in any of the items <1> to <19>, wherein the pore volume of the aluminum oxide catalyst is preferably 0.55 cm$^3$/g or more and 0.7 cm$^3$/g or less.

<21> The method for producing an olefin as set forth in any of the items <1> to <20>, wherein the BET specific surface area of the aluminum oxide catalyst is preferably 190 m$^2$/g or more, and more preferably 200 m$^2$/g or more, and it is preferably 500 m$^2$/g or less, more preferably 400 m$^2$/g or less, still more preferably 300 m$^2$/g or less, yet still more preferably 250 m$^2$/g or less, and even yet still more preferably 220 m$^2$/g or less.

<22> The method for producing an olefin as set forth in any of the items <1> to <21>, wherein the BET specific surface area of the aluminum oxide catalyst is preferably 190 m$^2$/g or more and 500 m$^2$/g or less.

<23> The method for producing an olefin as set forth in any of the items <1> to <22>, wherein the BET specific surface area of the aluminum oxide catalyst is preferably 190 m$^2$/g or more and 400 m$^2$/g or less.

<24> The method for producing an olefin as set forth in any of the items <1> to <23>, wherein the BET specific surface area of the aluminum oxide catalyst is preferably 200 m$^2$/g or more and 300 m$^2$/g or less.

<25> The method for producing an olefin as set forth in any of the items <1> to <24>, wherein the BET specific surface area of the aluminum oxide catalyst is preferably 200 m$^2$/g or more and 250 m$^2$/g or less.

<26> The method for producing an olefin as set forth in any of the items <1> to <25>, wherein the BET specific surface area of the aluminum oxide catalyst is preferably 200 m$^2$/g or more and 220 m$^2$/g or less.

<27> The method for producing an olefin as set forth in any of the items <1> to <26>, wherein the aluminum oxide catalyst is in the form of a powder, a granule, a noodle, or a pellet.

<28> The method for producing an olefin as set forth in any of the items <1> to <27>, wherein the aluminum oxide catalyst is in the form of a powder, and the average particle diameter of the powder is preferably 1 μm or more, more preferably 5 μm or more, still more preferably 10 μm or more, yet still more preferably 20 μm or more, and even yet still more preferably 30 μm or more, and it is preferably 300 μm or less, more preferably 250 μm or less, still more preferably 200 μm or less, yet still more preferably 150 μm or less, even yet still more preferably 100 μm or less, even still more preferably 50 μm or less, and even still more further preferably 37 μm or less.

<29> The method for producing an olefin as set forth in any of the items <1> to <27>, wherein the aluminum oxide catalyst is in the form of a granule, and the average particle diameter of the granule is preferably 0.2 mm or more, more preferably 0.4 mm or more, and still more preferably 0.6 mm or more, and it is preferably 2.0 mm or less, more preferably 1.3 mm or less, and still more preferably 0.8 mm or less.

<30> The method for producing an olefin as set forth in any of the items <1> to <27>, wherein the aluminum oxide catalyst is in a noodle-like form; its average diameter is preferably 1.0 mm or more, more preferably 1.2 mm or more, and still more preferably 1.4 mm or more, and it is preferably 2.5 mm or less, more preferably 2.0 mm or less, and still more preferably 1.5 mm or less; and its average length is preferably 8 mm or less, more preferably 6 mm or less, and still more preferably 4.5 mm or less, and it is preferably 2 mm or more, more preferably 3 mm or more, and still more preferably 3.5 mm or more.

<31> The method for producing an olefin as set forth in any of the items <1> to <27>, wherein the aluminum oxide catalyst is in a pellet-like form, and its average diameter and average height are each preferably 1.5 mm or more, more preferably 2.0 mm or more, and still more preferably 2.5 mm or more, and they are each preferably 5.0 mm or less, more preferably 4.0 mm or less, and still more preferably 3.0 mm or less.

<32> The method for producing an olefin as set forth in any of the items <1> to <31>, wherein the pore diameter of the aluminum oxide is preferably 5.0 nm or more, more preferably 6.0 nm or more, and still more preferably 8.0 nm or more, and it is preferably 25.0 nm or less, more preferably 20.0 nm or less, and still more preferably 18.0 nm or less.

<33> The method for producing an olefin as set forth in any of the items <1> to <32>, wherein the distribution range of the pore diameter of the aluminum oxide is preferably 5.0 nm or more and 25.0 nm or less, more preferably 6.0 nm or more and 20.0 nm or less, and still more preferably 8.0 nm or more and 18.0 nm or less.

<34> The method for producing an olefin as set forth in any of the items <1> to <33>, wherein the dehydration reaction is performed by a gas phase reaction or a liquid phase reaction, and preferably by a liquid phase reaction.

<35> The method for producing an olefin as set forth in any of the items <1> to <34>, wherein the dehydration reaction is performed by a suspension bed reaction or a fixed bed reaction, and preferably by a suspension bed reaction.

<36> The method for producing an olefin as set forth in any of the items <1> to <35>, wherein the dehydration reaction is performed preferably in an inert gas atmosphere or in a reducing atmosphere, more preferably in an inert gas atmosphere, still more preferably in an inert gas atmosphere of at least one selected from a helium gas, a nitrogen gas, and an argon gas, and yet still more preferably in a nitrogen gas atmosphere.

<37> The method for producing an olefin as set forth in any of the items <1> to <36>, wherein the dehydration reaction is a suspension bed reaction, and the reaction is performed while removing the produced water outside the reaction system by introducing an inert gas into the reaction system with stirring under reduced pressure of 0.03 MPa or more and 0.09 MPa or less, or at atmospheric pressure.

<38> The method for producing an olefin as set forth in any of the items <1> to <37>, wherein the dehydration reaction is a suspension bed reaction, and the amount of the aluminum oxide catalyst used is preferably 0.1 part by mass or more, more preferably 0.5 part by mass or more, still more preferably 1 part by mass or more, and yet still more preferably 2 parts by mass or more, and it is preferably 20 parts by mass or less, more preferably 15 parts by mass or less, still more preferably 10 parts by mass or less, and yet still more preferably 5 parts by mass or less, based on 100 parts by mass of the aliphatic alcohol.

<39> The method for producing an olefin as set forth in any of the items <1> to <38>, wherein the dehydration reaction is a suspension bed reaction, and the amount of the aluminum oxide catalyst used is preferably 0.1 part by mass or more and 20 parts by mass or less based on 100 parts by mass of the aliphatic alcohol.

<40> The method for producing an olefin as set forth in any of the items <1> to <39>, wherein the dehydration reaction is a suspension bed reaction, and the amount of the aluminum oxide catalyst used is preferably 0.5 part by mass or more and 15 parts by mass or less based on 100 parts by mass of the aliphatic alcohol.

<41> The method for producing an olefin as set forth in any of the items <1> to <40>, wherein the dehydration reaction is a suspension bed reaction, and the amount of the aluminum oxide catalyst used is preferably 1 part by mass or more and 10 parts by mass or less based on 100 parts by mass of the aliphatic alcohol.

<42> The method for producing an olefin as set forth in any of the items <1> to <41>, wherein the dehydration reaction is a suspension bed reaction, and the amount of the aluminum oxide catalyst used is preferably 2 parts by mass or more and 5 parts by mass or less based on 100 parts by mass of the aliphatic alcohol.

<43> The method for producing an olefin as set forth in any of the items <1> to <42>, wherein the dehydration reaction is a suspension bed reaction, and the reaction time is preferably 0.1 hour or more, more preferably 0.5 hour or more, and still more preferably 1 hour or more, and it is preferably 20 hours or less, more preferably 15 hours or less, and still more preferably 7 hours or less.

<44> The method for producing an olefin as set forth in any of the items <1> to <36>, wherein the dehydration reaction is a fixed bed reaction, and the LHSV (liquid hourly space velocity) is preferably 10/h or less, more preferably 7/h or less, still more preferably 5/h or less, and yet still more preferably 3/h or less, and it is preferably 0.03/h or more, more preferably 0.05/h or more, still more preferably 0.1/h or more, and yet still more preferably 0.2/h or more.

<45> The method for producing an olefin as set forth in any of the items <1> to <44>, wherein the reaction temperature of the dehydration reaction is preferably 200° C. or higher, more preferably 220° C. or higher, still more preferably 240° C. or higher, and yet still more preferably 260° C. or higher, and it is preferably 350° C. or lower, more preferably 330° C. or lower, still more preferably 310° C. or lower, and yet still more preferably 290° C. or lower.

<46> The method for producing an olefin as set forth in any of the items <1> to <45>, wherein the reaction temperature of the dehydration reaction is preferably 200° C. or higher and 350° C. or lower.

<47> The method for producing an olefin as set forth in any of the items <1> to <46>, wherein the reaction temperature of the dehydration reaction is preferably 220° C. or higher and 330° C. or lower.

<48> The method for producing an olefin as set forth in any of the items <1> to <47>, wherein the reaction temperature of the dehydration reaction is preferably 240° C. or higher and 310° C. or lower.

<49> The method for producing an olefin as set forth in any of the items <1> to <48>, wherein the reaction temperature of the dehydration reaction is preferably 260° C. or higher and 290° C. or lower.
<50> The method for producing an olefin as set forth in any of the items <1> to <49>, wherein the yield of the dimer is preferably 7% or less, and more preferably 5% or less.

EXAMPLES

[Measuring Method]
<Average Pore Diameter, Pore Volume, and BET Specific Surface Area>

The average pore diameter, the pore volume, and the BET specific surface area were measured by using a surface area and porosimetry analyzer "ASAP2020", manufactured by Micromeritics Instrument Corporation. After subjecting a sample to a heating pretreatment at 250° C. for 5 hours, the pore volume and the average pore diameter were calculated by the BJH method (Barrett-Joyner-Halenda method), and the pore diameter (diameter of the pore) of a peak top of the pore diameter distribution was designated as the average pore diameter. The BJH method is a method using, as a model, a cylindrical pore not connected to other pore, in which the pore distribution is determined by the capillary condensation and the multilayer adsorption of a nitrogen gas. The details thereof are described in "Shimadzu Review", vol. 48, No. 1, pp. 35-44 (1991). In the case where plural peaks appear in the pore diameter distribution, the pore diameter of the maximum peak top is designated as the average pore diameter. In addition, when plural peak tops having the same height appear, the average pore diameter are determined in the following manner 1 or 2.

1. In the case where the pore diameter of any one of the peak tops having the same height is 12.5 nm or more and 20.0 nm or less, a minimum value of the pore diameter of the peak tops of 12.5 nm or more and 20.0 nm or less is designated as the average pore diameter.

2. In the case where the pore diameter of all of the peak tops having the same height does not fall within the range of 12.5 nm or more and 20.0 nm or less, a minimum value of the pore diameter of the peak tops is designated as the average pore diameter.

As for the BET specific surface area, after performing the same pretreatment, it was measured by the multi-point method using liquid nitrogen to provide a value within a range where the parameter C was positive.

<Average Particle Diameter>

As for the average particle diameter of the aluminum oxide catalyst, the measurement was performed with a laser diffraction/scattering particle size distribution analyzer "LA-920" (manufactured by Horiba, Ltd.) by dispersing 0.05 g of the catalyst in ethanol (Cica-First Grade Reagent, manufactured by Kanto Chemical Co., Inc.) as a measuring solvent while stirring (stirring rate: level 4), and a median diameter was calculated assuming that the refractive index was 1.10.

Catalyst Preparation Example 1

In a 2-liter separable flask, 500 g of ion-exchanged water and 100 g of a 30% by mass aluminum chloride hexahydrate aqueous solution (prepared by diluting a reagent, manufactured by Wako Chemical Industries, Ltd. with ion-exchanged water) were charged, and the temperature was raised to 90° C. while stirring. Thereafter, 51.7 g of 28% by mass ammonia water (manufactured by Wako Chemical Industries, Ltd.) was collectively added. After stirring for 5 minutes, 131.6 g of a 30% by mass aluminum chloride hexahydrate aqueous solution was added. After further stirring for 5 minutes, 71.7 g of 28% by mass ammonia water was added. A suspension liquid A thus obtained was filtered and dried at 120° C., and the resultant was calcined in air at 500° C. for 3 hours, thereby preparing a catalyst A in the form of a powder.

The resulting aluminum oxide catalyst A had a BET specific surface area of 164 $m^2/g$, an average particle diameter of 35 μm, an average pore diameter of 10.5 nm, and a pore volume of 0.41 $cm^3/g$.

Catalyst Preparation Example 2

To the aforementioned suspension liquid A, 317.5 g of a 30% by mass aluminum chloride hexahydrate aqueous solution was added at 90° C. and stirred for 5 minutes, and 137.0 g of 28% by mass ammonia water was added and stirred for 5 minutes, thereby obtaining a suspension liquid B. 809.0 g of the suspension liquid B was recovered and subjected to the same post-treatment as in the catalyst A, thereby obtaining a catalyst B in the form of a powder.

The resulting aluminum oxide catalyst B had a BET specific surface area of 231 $m^2/g$, an average particle diameter of 31 μm, an average pore diameter of 12.8 nm, and a pore volume of 0.61 $cm^3/g$.

Catalyst Preparation Example 3

To the remaining suspension liquid B as mentioned above, 317.5 g of a 30% by mass aluminum chloride hexahydrate aqueous solution was added at 90° C. and stirred for 5 minutes, and 95.6 g of 28% by mass ammonia water was added and stirred for 5 minutes. Furthermore, 375.5 g of a 30% by mass aluminum chloride hexahydrate aqueous solution was added and stirred for 5 minutes, and 165.7 g of 28% by mass ammonia water was added and stirred for 5 minutes, thereby obtaining a suspension liquid C. 1,056 g of the suspension liquid C was recovered and subjected to the same post-treatment as in the catalyst A, thereby obtaining a catalyst C in the form of a powder.

The resulting aluminum oxide catalyst C had a BET specific surface area of 212 $m^2/g$, an average particle diameter of 32 μm, an average pore diameter of 13.4 nm, and a pore volume of 0.64 $cm^3/g$.

Catalyst Preparation Example 4

To the remaining suspension liquid C as mentioned above, 70.3 g of a 30% by mass aluminum chloride hexahydrate aqueous solution was added at 90° C. and stirred for 5 minutes, and 45.4 g of 28% by mass ammonia water was added and stirred for 5 minutes. Furthermore, 163.2 g of a 30% by mass aluminum chloride hexahydrate aqueous solution was added and stirred for 5 minutes, and 83.9 g of 28% by mass ammonia water was added and stirred for 5 minutes. Furthermore, 300.5 g of a 30% by mass aluminum chloride hexahydrate aqueous solution was added and stirred for 5 minutes, and 156.7 g of 28% by mass ammonia water was added and stirred for 5 minutes, thereby obtaining a suspension liquid D.

607.3 g of the suspension liquid D was recovered and subjected to the same post-treatment as in the catalyst A, thereby obtaining a catalyst D in the form of a powder.

The resulting aluminum oxide catalyst D had a BET specific surface area of 205 m²/g, an average particle diameter of 35 μm, an average pore diameter of 15.1 nm, and a pore volume of 0.66 cm³/g.

Catalyst Preparation Example 5

To the remaining suspension liquid D as mentioned above, 152.1 g of a 30% by mass aluminum chloride hexahydrate aqueous solution was added at 90° C. and stirred for 5 minutes, and 96.7 g of 28% by mass ammonia water was added and stirred for 5 minutes. Furthermore, 367.8 g of a 30% by mass aluminum chloride hexahydrate aqueous solution was added and stirred for 5 minutes, and 179.1 g of 28% by mass ammonia water was added and stirred for 5 minutes. The resulting suspension liquid was subjected to the same post-treatment as in the catalyst A, thereby obtaining a catalyst E in the form of a powder.

The resulting aluminum oxide catalyst E had a BET specific surface area of 201 m²/g, an average particle diameter of 36 μm, an average pore diameter of 17.6 nm, and a pore volume of 0.59 cm³/g.

Catalyst F

Aluminum oxide, gamma-phase (manufactured by Alfa Aesar) was used as a catalyst F.

The aluminum oxide catalyst F had a BET specific surface area of 165 m²/g, an average particle diameter of 38 μm, an average pore diameter of 8.7 nm, and a pore volume of 0.35 cm³/g.

Catalyst G

GP-20 (γ-Al₂O₃, produced by Mizusawa Industrial Chemicals, Ltd.) was used as a catalyst G.

The aluminum oxide catalyst G had a BET specific surface area of 189 m²/g, an average particle diameter of 26 μm, an average pore diameter of 12.1 nm, and a pore volume of 0.50 cm³/g.

The BET specific surface area, the average particles diameter, the average pore diameter, and the pore volume of each of the catalysts A to G are shown in the following Table 1.

TABLE 1

|  | BET specific surface area m²/g | Average particle diameter μm | Average pore diameter nm | Pore volume cm³/g |
|---|---|---|---|---|
| Catalyst A | 164 | 35 | 10.5 | 0.41 |
| Catalyst B | 231 | 31 | 12.8 | 0.61 |
| Catalyst C | 212 | 32 | 13.4 | 0.64 |
| Catalyst D | 205 | 35 | 15.1 | 0.66 |
| Catalyst E | 201 | 36 | 17.6 | 0.59 |
| Catalyst F | 165 | 38 | 8.7 | 0.35 |
| Catalyst G | 189 | 26 | 12.1 | 0.50 |

Example 1 [Olefination Reaction]

In a 100-mL four-necked flask equipped with a stirrer, 50.0 g (0.19 mol) of 1-octadecanol "KALCOL 8098" (manufactured by Kao Corporation) and 1.5 g (3 parts by mass based on 100 parts by mass of the alcohol) of the aluminum oxide catalyst B prepared in Catalyst Preparation Example 2 were charged and allowed to react with each other at 280° C. under stirring while flowing nitrogen through the reaction system (nitrogen flow rate: 50 mL/min).

After the temperature of the reaction system reached the reaction temperature (280° C.), sampling was carried out at intervals of 30 minutes, and the reaction behavior was followed by means of gas chromatography (GC), thereby confirming a time required for which the conversion reached 100%. Here, the fact that the conversion was 100% means that GC signals of the raw material alcohol and the intermediate ether were not detected. The reaction time shown in Table 2 means the reaction time until the conversion reached 100%.

When the conversion reached 100%, the reaction was terminated. The solution after termination of the reaction was diluted with hexane and quantitatively determined for the products through an analysis with a gas chromatography analyzer "HP6890" (manufactured by Hewlett-Packard Company) equipped with a column "Ultra ALLOY-1" (capillary column: 30.0 m×250 μm, manufactured by Frontier Laboratories Ltd.) and a hydrogen flame ionization detector (FID) under a condition at an injection temperature of 300° C., a detector temperature of 350° C., and a He flow rate of 4.6 mL/min. The results are shown in Table 2.

The olefin yield was calculated according to the following expression. In addition, a value obtained by subtracting the olefin yield (%) from 100% was designated as the dimer yield.

Olefin yield (%)=[(Amount of olefin (mol))/(Charged amount of raw material alcohol (mol))]×100

Examples 2 to 6 and Comparative Examples 1 to 5 [Olefination Reaction]

The reaction was performed in the same manner as in Example 1, except for changing the catalyst and the raw material alcohol used and the reaction condition as shown in Table 2, and the solutions after termination of the reaction were measured. The catalyst and the raw material alcohol used, the reaction condition, and the results are collectively shown in Table 2. In Table 2, "Octadecanol" is "1-octadecanol", and "Hexadecanol" is "1-hexadecanol".

In addition, the results of Examples 1 to 4 and Comparative Examples 1 to 3 are shown in FIG. 1.

TABLE 2

|  | Unit | Example 1 | Example 2 | Example 3 | Example 4 | Comparative Example 1 | Comparative Example 2 | Comparative Example 3 | Example 5 | Comparative Example 4 | Example 6 | Comparative Example 5 |
|---|---|---|---|---|---|---|---|---|---|---|---|---|
| Catalyst | — | B | C | D | E | F | A | G | B | G | B | G |
| Average pore diameter | nm | 12.8 | 13.4 | 15.1 | 17.6 | 8.7 | 10.5 | 12.1 | 12.8 | 12.1 | 12.8 | 12.1 |

TABLE 2-continued

| | Unit | Example 1 | Example 2 | Example 3 | Example 4 | Comparative Example 1 | Comparative Example 2 | Comparative Example 3 | Example 5 | Comparative Example 4 | Example 6 | Comparative Example 5 |
|---|---|---|---|---|---|---|---|---|---|---|---|---|
| Raw material alcohol | — | Octadecanol | | | | Octadecanol | | | Octadecanol | | Hexadecanol | |
| Amount of catalyst | parts by mass* | 3 | 3 | 3 | 3 | 3 | 3 | 3 | 10 | 10 | 3 | 3 |
| Reaction temperature | °C. | 280 | 280 | 280 | 280 | 280 | 280 | 280 | 240 | 240 | 280 | 280 |
| Reaction time | hr | 4.0 | 3.0 | 2.5 | 3.0 | 9.0 | 8.0 | 7.0 | 13 | 20 | 3.5 | 6.0 |
| Conversion | % | 100.0 | 100.0 | 100.0 | 100.0 | 100.0 | 100.0 | 100.0 | 100.0 | 100.0 | 100.0 | 100.0 |
| Olefin yield | % | 95.8 | 95.4 | 97.0 | 96.0 | 91.5 | 95.5 | 94.5 | 93.9 | 92.8 | 96.0 | 95.2 |
| Dimer yield | % | 4.2 | 4.6 | 3.0 | 4.0 | 8.5 | 4.5 | 5.5 | 6.1 | 7.2 | 4.0 | 4.8 |

*Amount of catalyst based on 100 parts by mass of raw material alcohol

From the results of Table 2 and FIG. 1, it has become clear that in Examples 1 to 6 each using the aluminum oxide catalyst having an average pore diameter of 12.5 nm or more and 20.0 nm or less, the reaction time required for which the conversion of the raw material alcohol reaches 100% is short, the yield of the dimer that is a by-product is low, the reactivity is excellent, and the formation of by-products is suppressed, as compared with Comparative Examples 1 to 5 each using the aluminum oxide catalyst having an average pore diameter of less than 12.5 nm.

In the light of the above, in accordance with the production method of the present invention, the olefin can be produced with a high yield for a short reaction time.

INDUSTRIAL APPLICABILITY

In accordance with the present invention, in a method for producing an olefin through a dehydration reaction of an aliphatic alcohol having 6 or more carbon atoms, the olefin can be produced with a high yield for a short reaction time. The olefin obtained by the present invention is useful as a raw material or an intermediate of a surfactant, an organic solvent, a softener, a sizing agent, and the like.

The invention claimed is:

1. A method for producing an olefin, comprising subjecting an aliphatic alcohol having 6 or more carbon atoms to a dehydration reaction in the presence of a catalyst consisting of aluminum oxide, wherein
    an average pore diameter of the catalyst is 12.5 nm or more and 20.0 nm or less, and
    the catalyst is a powdered or granulated aggregate or is combined with a binder and molded.

2. The method for producing an olefin according to claim 1, wherein the carbon number of the aliphatic alcohol is 8 or more and 22 or less.

3. The method for producing an olefin according to claim 1, wherein the carbon number of the aliphatic alcohol is 14 or more and 18 or less.

4. The method for producing an olefin according to claim 1, wherein the aliphatic alcohol is a primary alcohol.

5. The method for producing an olefin according to claim 1, wherein the aliphatic alcohol is a straight-chain aliphatic alcohol.

6. The method for producing an olefin according to claim 1, wherein the aliphatic alcohol is a saturated straight-chain aliphatic alcohol.

7. The method for producing an olefin according to claim 1, wherein the amount of the catalyst used is 0.1 to 20 parts by mass based on 100 parts by mass of the aliphatic alcohol.

8. The method for producing an olefin according to claim 1, wherein the catalyst is γ-alumina.

9. The method for producing an olefin according to claim 1, wherein the average pore diameter of the catalyst is 13.0 nm or more and 20.0 nm or less.

10. The method for producing an olefin according to claim 1, wherein the average pore diameter of the catalyst is 13.0 nm or more and 18.0 nm or less.

11. The method for producing an olefin according to claim 1, wherein the average pore diameter of the catalyst is 13.5 nm or more and 16.0 nm or less.

12. The method for producing an olefin according to claim 1, wherein a pore volume of the catalyst is more than 0.50 $cm^3/g$ and 2.0 $cm^3/g$ or less.

13. The method for producing an olefin according to claim 1, wherein a BET specific surface area of the catalyst is 190 $m^2/g$ or more and 500 $m^2/g$ or less.

14. The method for producing an olefin according to claim 1, wherein the dehydration reaction is performed at 200° C. or higher and 350° C. or lower.

15. The method for producing an olefin according to claim 1, wherein the dehydration reaction is performed by a liquid phase reaction.

16. The method for producing an olefin according to claim 1, wherein the dehydration reaction is performed in an inert gas atmosphere or a reducing atmosphere.

* * * * *